(12) United States Patent
Lee et al.

(10) Patent No.: US 7,312,181 B2
(45) Date of Patent: Dec. 25, 2007

(54) ACYLATED THIOSEMICARBAZIDES AS HERBICIDES

(75) Inventors: Shy-Fuh Lee, Sunnyvale, CA (US); Vivian Du, Phoenix, AZ (US); Richard Anderson, Palo Alto, CA (US)

(73) Assignee: Cropsolution, Inc., Morrisville, NC (US)

( * ) Notice: Subject to any disclaimer, the term of this patent is extended or adjusted under 35 U.S.C. 154(b) by 23 days.

(21) Appl. No.: 11/386,499

(22) Filed: Mar. 22, 2006

(65) Prior Publication Data

US 2006/0229206 A1    Oct. 12, 2006

Related U.S. Application Data

(60) Provisional application No. 60/669,733, filed on Apr. 8, 2005.

(51) Int. Cl.
  *A01N 43/40*   (2006.01)
  *C07D 213/46*  (2006.01)
(52) U.S. Cl. .................. 504/244; 504/289; 504/294; 504/328; 546/314; 549/70; 549/498; 564/18
(58) Field of Classification Search ................ 504/244, 504/289, 298, 335, 294, 328; 546/314; 564/74, 564/18; 549/70, 498
  See application file for complete search history.

(56) References Cited

U.S. PATENT DOCUMENTS 5,561,101 A    10/1996 Anderson et al.

6,838,415 B1    1/2005 Muller et al.
6,861,389 B2    3/2005 Giencke et al.
2002/0127605 A1    9/2002 Hamilton et al.

FOREIGN PATENT DOCUMENTS

WO    WO 02/44126 A2    6/2002
WO    WO 02/059080 A2    8/2002

OTHER PUBLICATIONS

Notification of Transmittal of International Search Report and Written Opinion of the International Searching Authority; date of mailing Nov. 8, 2006.

*Primary Examiner*—Zinna N. Davis
(74) *Attorney, Agent, or Firm*—Myers Bigel Sibley & Sajovec, P.A.

(57) ABSTRACT

The present invention provides compounds of Formula I:

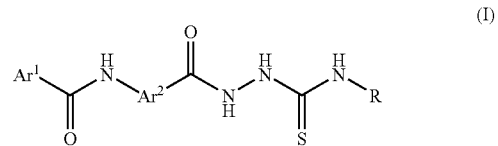

wherein $Ar^1$ is aryl or heteroaryl, $Ar^2$ is aryl or heteroaryl, and R is a suitable organic group. Herbicidal composition comprising such active compounds, and methods for controlling undesirable plants by applying such compounds, are also described.

46 Claims, No Drawings

ACYLATED THIOSEMICARBAZIDES AS HERBICIDES

RELATED APPLICATIONS

This application claims the benefit of U.S. Provisional Patent Application No. 60/669,733, filed Apr. 8, 2005, the disclosure of which is incorporated by reference herein in its entirety.

FIELD OF THE INVENTION

The present invention concerns acylated thiosemicarbazides, methods of making the same, compositions containing the same, and methods of using such compounds, particularly as herbicides.

BACKGROUND OF THE INVENTION

PCT Application WO 02/044126 to G. Hamilton et al. describes bisubstituted carbocyclic cyclophilin binding compounds for use in certain medical disorders. Compounds 32, 33, 37, 38 and 41 therein are as follows:

PCT Application WO 02/059080 to Wu et al. describes trisubstituted carbocyclic cyclophilin binding compounds for use in certain medical disorders. Compound 53 therein is as follows:

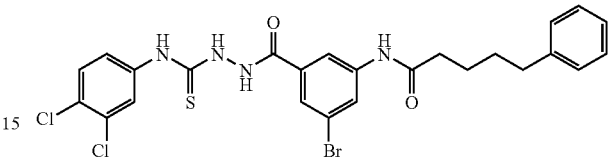

53

SUMMARY OF THE INVENTION

A first aspect of the present invention is compounds or active compounds of Formula I:

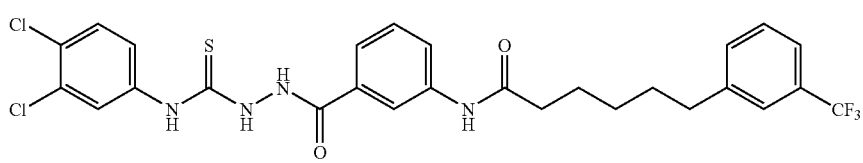

32

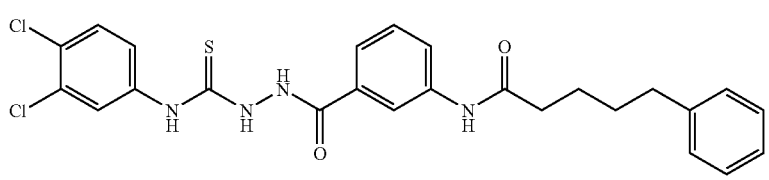

33

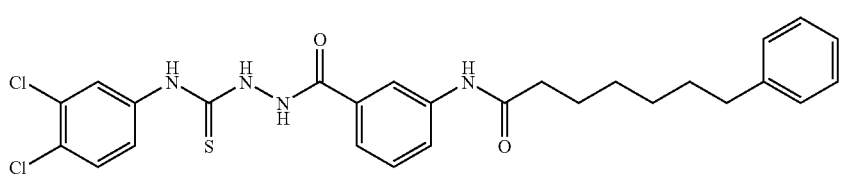

37

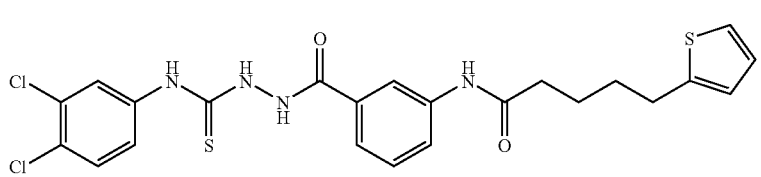

38

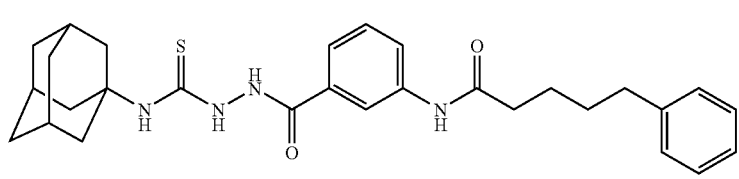

41

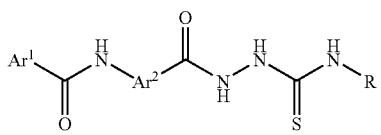

wherein:

Ar$^1$ is aryl which may be substituted 1, 2, 3, 4 or 5 times with halogen, alkyl, alkenyl, alkynyl, haloalkyl, haloalkenyl, haloalkynyl, alkoxy, alkylthio, haloalkoxy, haloalkylthio, cyano, nitro; or Ar$^1$ is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro (independently selected at each position), Ar$^2$ is aryl which may be unsubstituted or optionally substituted 1, 2, 3, or 4 times with halogen, alkyl, alkenyl, alkynyl, haloalkyl, haloalkenyl, haloalkynyl, alkoxy, alkylthio, haloalkoxy, haloalkylthio, cyano, or nitro; or Ar$^2$ is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro, R is alkyl, alkenyl, alkynyl, haloalkyl, haloalkenyl, haloalkynyl, acyl, or alkoxycarbonyl, or aryl optionally substituted with halogen, alkyl, alkenyl, alkynyl, haloalkyl, haloalkenyl, haloalkynyl, alkoxy, alkylthio, haloalkoxy, haloalkylthio, cyano, or nitro; or R is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro;

or a salt thereof.

A further aspect of the invention is a herbicidal composition comprising at least one active compound as described herein in combination with an extender or surfactant.

A further aspect of the invention is a method for controlling undesirable plants comprising applying an effective amount of an active compound as described herein to said plants or a habitat of said plants.

The foregoing and other objects and aspects of the present invention are explained in greater detail below.

DETAILED DESCRIPTION OF THE PREFERRED EMBODIMENTS

"Alkyl" as used herein refers to a saturated hydrocarbon radical which may be straight-chain or branched-chain (for example, ethyl, isopropyl, t-amyl, or 2,5-dimethylhexyl) or cyclic (for example cyclobutyl, cyclopropyl or cyclopentyl) and contains from 1 to 24 carbon atoms. This definition applies both when the term is used alone and when it is used as part of a compound term, such as "haloalkyl" and similar terms. In some embodiments, preferred alkyl groups are those containing 1 to 4 carbon atoms, which are also referred to as "lower alkyl." In some embodiments preferred alkyl groups are those containing 5 or 6 to 24 carbon atoms, which may also be referred to as "higher alkyl".

"Alkenyl," as used herein, refers to a straight or branched chain hydrocarbon containing from 2 to 24 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 24 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

"Alkoxy" refers to an alkyl radical as described above which also bears an oxygen substituent which is capable of covalent attachment to another hydrocarbon radical (such as, for example, methoxy, ethoxy and t-butoxy).

"Alkylthio" as used herein refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" or "aromatic ring moiety" refers to an aromatic substituent which may be a single ring or multiple rings which are fused together, linked covalently or linked to a common group such as an ethylene or methylene moiety. The aromatic rings may each contain heteroatoms and hence "aryl" encompasses "heteroaryl" as used herein. Representative examples of aryl include, azulenyl, indanyl, indenyl, naphthyl, phenyl, tetrahydronaphthyl, biphenyl, diphenylmethyl, 2,2-diphenyl-1-ethyl, thienyl, pyridyl and quinoxalyl. "Aryl" means substituted or unsubstituted aryl unless otherwise indicated and hence the aryl moieties may be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible. For example, the heteroatom S may be substituted with one or two oxo groups, which may be shown as =O.

"Agriculturally acceptable salt" means a salt the cation of which is known and accepted in the art for the formation of salts for agricultural or horticultural use. Preferably the salts are water-soluble.

"Cyano" as used herein refers to a —CN group.

"Halo" or "halogen," as used herein, refers to —Cl, —Br, —I or —F.

"Haloalkyl," "haloalkenyl", "haloalkynyl", "haloalkoxy", "haloalkylthio", etc. as used herein, refers to at least one halogen, as defined herein, appended to the parent molecular moiety through an alkyl, alkenyl, alkynyl, alkoxy, or alkylthio group, respectively, as defined herein. Representative examples of haloalkyl include, but are not limited to, chloromethyl, 2-fluoroethyl, trifluoromethyl, pentafluoroethyl, 2-chloro-3-fluoropentyl, and the like.

"Hydroxy," as used herein, refers to an —OH group.

"Nitro," as used herein, refers to a —NO$_2$ group.

"Oxy," as used herein, refers to a —O— moiety.

"Thio," as used herein, refers to a —S— moiety.

The disclosures of all US Patent references cited herein are to be incorporated herein in their entirety as if fully set forth.

2. Compounds. The compounds this invention (sometimes referred to as "active compounds" or "active agents" herein) are represented by Formula I:

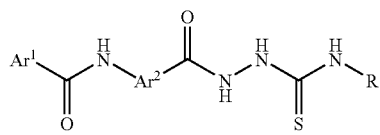

(I)

wherein:

Ar$^1$ is aryl optionally substituted 1, 2, 3, 4 or 5 times with halogen, alkyl, alkenyl, alkynyl, haloalkyl, haloalkenyl, haloalkynyl, alkoxy, alkylthio, haloalkoxy, haloalkylthio, cyano, nitro, or aryl or heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro; or Ar$^1$ is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, nitro, or aryl or heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro, (independently selected at each position), Ar$^2$ is aryl which may be unsubstituted or optionally substituted 1, 2, 3, or 4 times with halogen, alkyl, alkenyl, alkynyl, haloalkyl, haloalkenyl, haloalkynyl, alkoxy, alkylthio, haloalkoxy, haloalkylthio, cyano, or nitro; or Ar$^2$ is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro, R is alkyl, alkenyl, alkynyl, haloalkyl, haloalkenyl, haloalkynyl, acyl, or alkoxycarbonyl, or aryl optionally substituted with halogen, alkyl, alkenyl, alkynyl, haloalkyl, haloalkenyl, haloalkynyl, alkoxy, alkylthio, haloalkoxy, haloalkylthio, cyano, or nitro; or R is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro;

or a salt thereof.

Examples of Ar$^1$ in compounds of Formula I are:

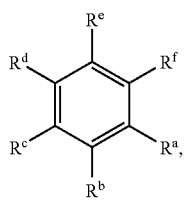 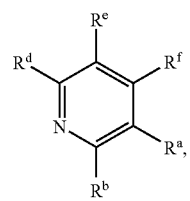

-continued

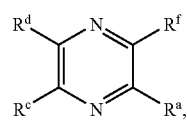 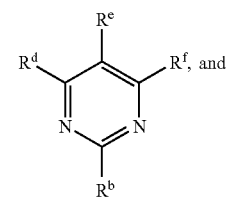

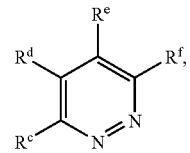

where R$^a$, R$^b$, R$^c$, R$^d$, R$^e$, and R$^f$ are each independently H, halogen, alkyl, alkenyl, alkynyl, haloalkyl, haloalkenyl, haloalkynyl, alkoxy, alkylthio, haloalkoxy, haloalkylthio, cyano, nitro; or aryl or heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro, or where two of the R$^a$, R$^b$, R$^c$, R$^d$, R$^e$, and R$^f$ are taken together to form another 5 or 6 membered ring containing C, N, O and/or S atoms, optionally substituted with halogen, alkyl, alkenyl, alkynyl, haloalkyl, haloalkenyl, haloalkynyl, alkoxy, alkylthio, haloalkoxy, haloalkylthio, cyano, or nitro, subject to the proviso that one of R$^a$, R$^b$, R$^c$, R$^d$, R$^e$, and R$^f$ is a covalent bond to the adjacent carbonyl carbon;

as well as five membered heteroaromatic rings containing 1, 2, or 3 heteroatoms selected from the group consisting of N, O, and S, which heteroaromatic rings may be unsubstituted or substituted in like manner as above, examples of which are:

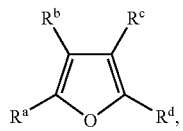 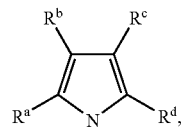

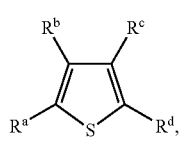 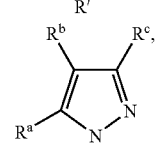

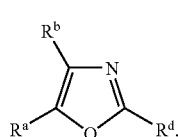 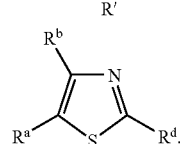

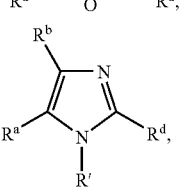 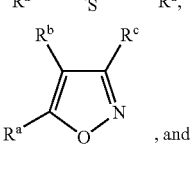

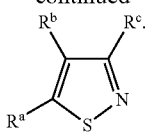

where $R^a$, $R^b$, $R^c$ and $R^d$ are, when present, each independently H, halogen, alkyl, alkenyl, alkynyl, haloalkyl, haloalkenyl, haloalkynyl, alkoxy, alkylthio, haloalkoxy, haloalkylthio, cyano, nitro, or aryl or heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro, or where two of the $R^a$, $R^b$, $R^c$, and $R^d$ are taken together to form another 5 or 6 membered ring containing C, N, O and/or S atoms, optionally substituted with halogen, alkyl, alkenyl, alkynyl, haloalkyl, haloalkenyl, haloalkynyl, alkoxy, alkylthio, haloalkoxy, haloalkylthio, cyano, or nitro;

subject to the proviso that one of $R^a$, $R^b$, $R^c$ or $R^d$ is a covalent bond to the adjacent carbonyl carbon, and R' is, when present, H or alkyl Examples of $Ar^2$ in compounds of Formula I are:

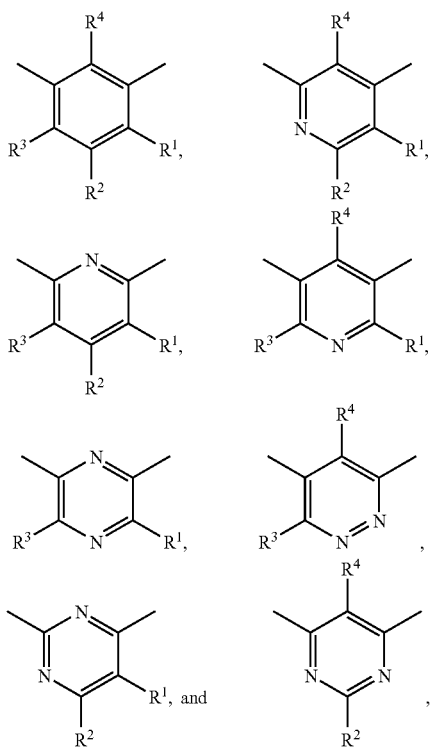

where $R^1$, $R^2$, $R^3$ and $R^4$ are, when present, each independently H, halogen, alkyl, alkenyl, alkynyl, haloalkyl, haloalkenyl, haloalkynyl, alkoxy, alkylthio, haloalkoxy, haloalkylthio, cyano, or nitro.

as well as five membered heteroaromatic rings containing 1, 2, or 3 heteroatoms selected from the group consisting of N, O, and S, which heteroaromatic rings may be unsubstituted or substituted in like manner as above, examples of which are:

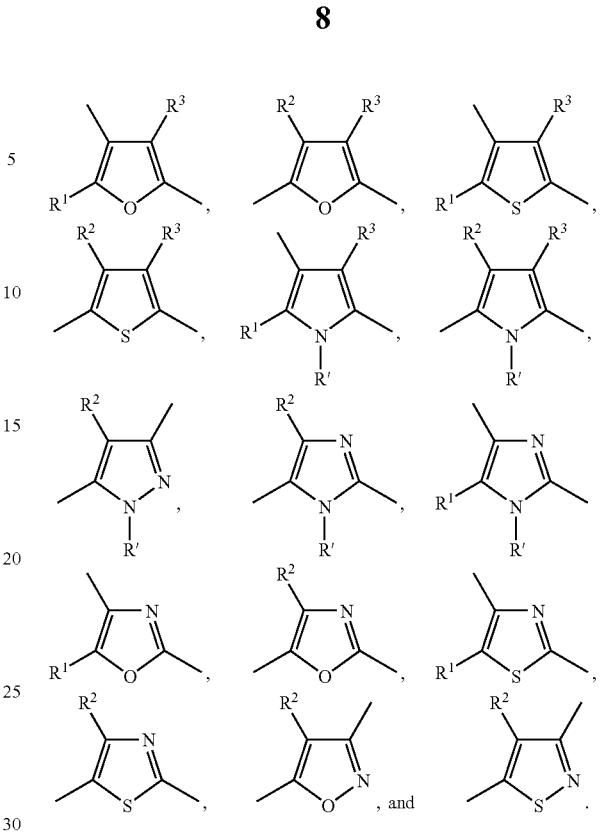

where $R^1$, $R^2$, and $R^3$ are, when present, each independently H, halogen, alkyl, alkenyl, alkynyl, haloalkyl, haloalkenyl, haloalkynyl, alkoxy, alkylthio, haloalkoxy, haloalkylthio, cyano, or nitro, R' is, when present, H or alkyl.

A particular example of compounds of Formula I is, accordingly, compounds of Formula Ia:

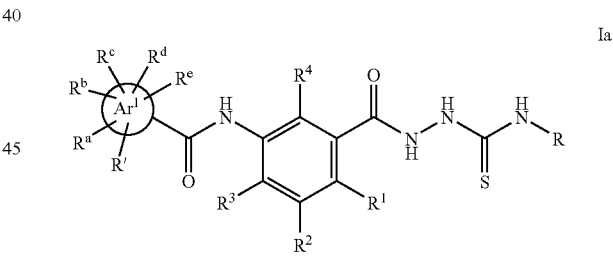

wherein:

$Ar^1$ is a five or six-membered aromatic ring selected from phenyl, pyridyl, pyrimidinyl, pyrazinyl, pyridazinyl, furyl, thienyl, oxazolyl, thiazolyl, isoxazolyl, isothiazolyl, pyrrolyl, imidazolyl, or pyazolyl (which may be in any orientation);

where $R^a$, $R^b$, $R^c$, $R^d$, and $R^e$ are, when present, each independently H, halogen, alkyl, alkenyl, alkynyl, haloalkyl, haloalkenyl, haloalkynyl, alkoxy, alkylthio, haloalkoxy, haloalkylthio, cyano, nitro, or aryl or heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro;

or where two of the $R^a$, $R^b$, $R^c$, $R^d$, and $R^e$ are taken together to form another 5 or 6 membered ring containing C, N, O and/or S atoms, optionally substituted with halogen, alkyl, alkenyl, alkynyl, haloalkyl, haloalkenyl, haloalkynyl, alkoxy, alkylthio, haloalkoxy, haloalkylthio, cyano, or nitro, R' is, when present, H or alkyl, and R is alkyl, alkenyl, alkynyl, haloalkyl, haloalkenyl, haloalkynyl, acyl, or alkoxycarbonyl, or aryl optionally substituted with halogen, alkyl, alkenyl, alkynyl, haloalkyl, haloalkenyl, haloalkynyl, alkoxy, alkylthio, haloalkoxy, haloalkylthio, cyano, or nitro; or R is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro;

$R^1$, $R^2$, $R^3$ and $R^4$ are, when present, each independently H, halo, alkyl, alkenyl, alkynyl, haloalkyl, haloalkenyl, haloalkynyl, alkoxy, alkylthio, haloalkoxy, haloalkylthio, or nitro;

or a salt thereof.

$Ar^1$ in Formula Ia can be any of the rings shown above for $Ar^1$, with the covalent bond to the adjacent carbonyl carbon at any position on the ring. Thus, examples of compounds of Formula Ia includes compounds of Formulas Ib-Ii below:

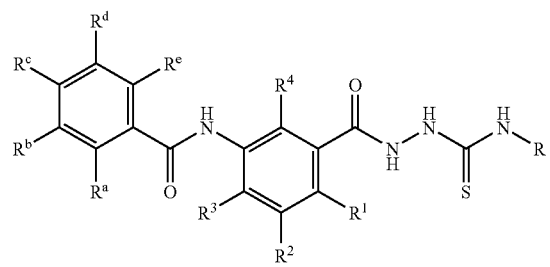
(Ib)

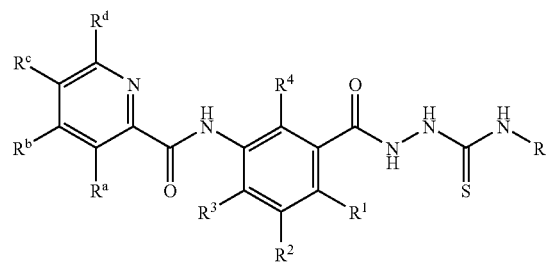
(Ic)

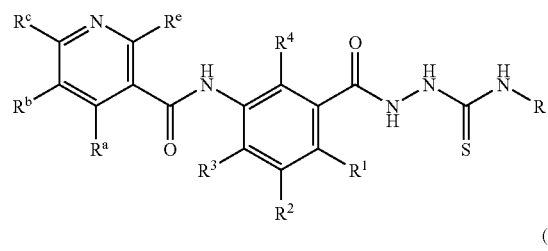
(Id)

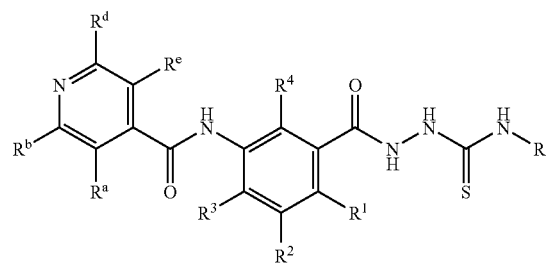
(Ie)

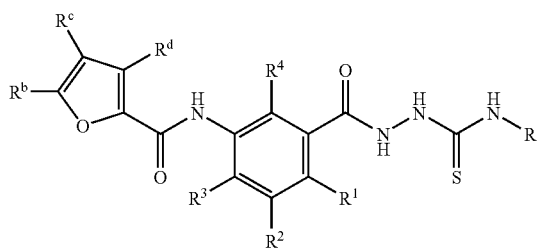
(If)

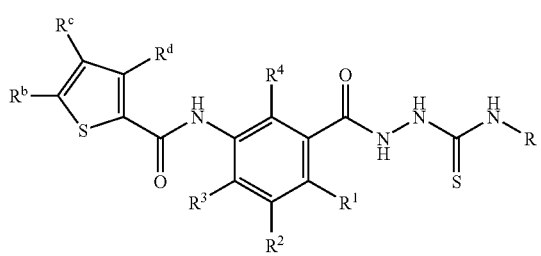
(Ig)

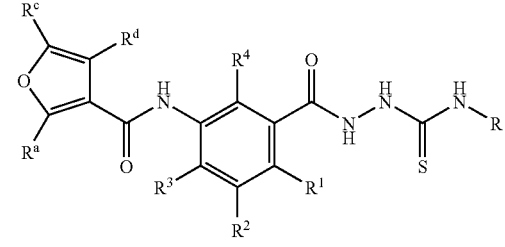
(Ih)

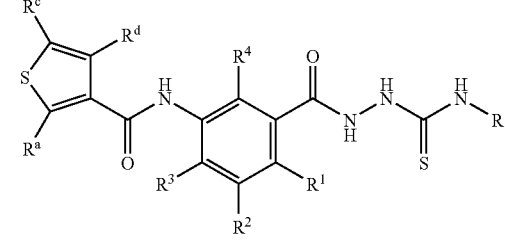
(Ii)

Of course, any of the other rings shown for $Ar^1$ or $Ar^2$ above can be substituted into compounds of Formulas I-Ii above in like manner.

The compounds and compositions in the invention are useful as crop protection agents to control weeds or unwanted vegetation, to combat or prevent fungal infestations, or to control insects, or acarids that are harmful to crops.

Compounds of Formula I may be prepared as outlined in Scheme 1 or variations thereof that will be apparent to those skilled in the art. An amino substituted methyl arylcarboxylate ($H_2NAr_2COOMe$) is acylated with an aryl acid chloride ($Ar_1COCl$) in the presence of an amine such as triethylamine (TEA) to give ester amide II. Treatment of II with hydrazine in THF gives the hydrazide III, which upon treatment with a substituted isothiocyanate RNCS, produces the title compounds of the Formula I.

Scheme 1

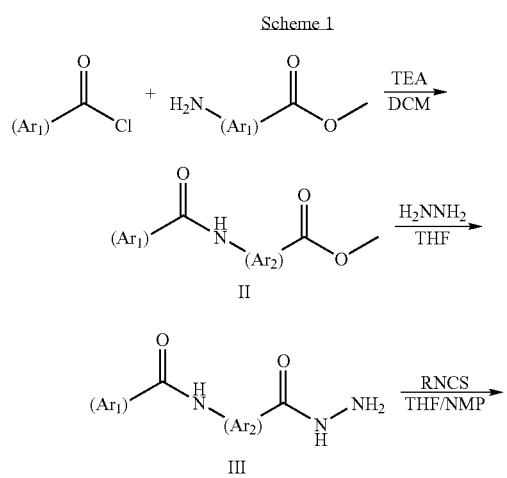

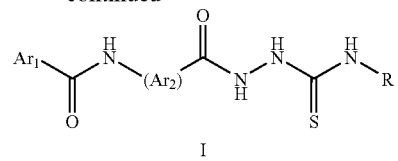

I

Compositions that are especially useful for the control of undesired plant growth are those in which:

Ar$_1$ is aryl optionally substituted with halogen, alkyl, alkynyl, haloalkyl, alkoxy, alkylthio, haloalkoxy, cyano, or nitro;

Ar$_2$ is aryl optionally substituted with halogen, alkyl, haloalkyl, alkoxy, alkylthio, haloalkoxy; or heteroaryl, especially pyridyl, optionally substituted with halogen, alkyl, haloalkyl, alkoxy, alkylthio, or haloalkoxy, R is aryl optionally substituted with halogen, alkyl, alkynyl, haloalkyl, alkoxy, alkylthio, haloalkoxy, cyano, or nitro.

Examples of compounds of the present invention include, but are not limited to, the following:

| | Structure | Chemical Name |
|---|---|---|
| 1 | 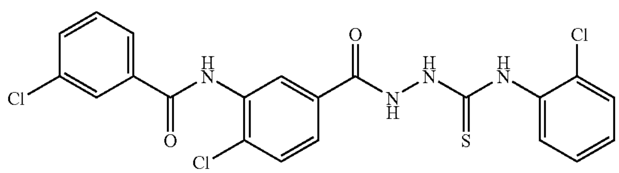 | 1-[4-Chloro-3-(3-chloro-benzamido)-benzoyl]-4-(2-chlorophenyl)-thiosemicarbazide |
| 2 | 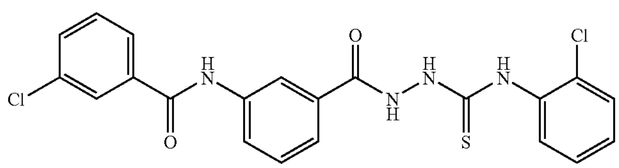 | 1-[3-(3-Chlorobenzamido)-benzoyl]-4-(2-chlorophenyl)-thiosemicarbazide |
| 3 | 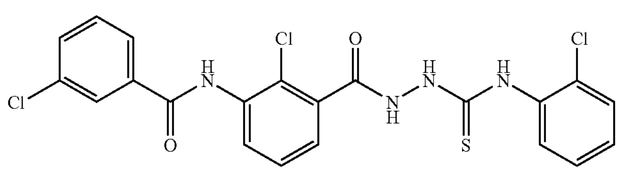 | 1-[2-Chloro-3-(3-chloro-benzamido)-benzoyl]-4-(2-chlorophenyl)-thiosemicarbazide |
| 4 | 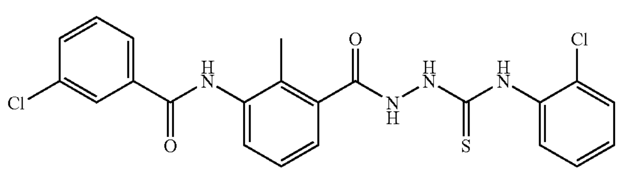 | 1-[3-(3-Chlorobenzamido)-2-methylbenzoyl]-4-(2-chloro-phenyl)-thiosemicarbazide |
| 5 | 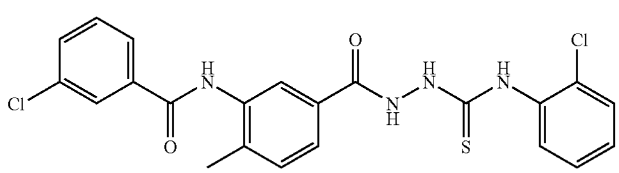 | 1-[3-(3-Chlorobenzamido)-4-methylbenzoyl]-4-(2-chlorophenyl)-thiosemicarbazide |

-continued

| | Structure | Chemical Name |
|---|---|---|
| 6 | 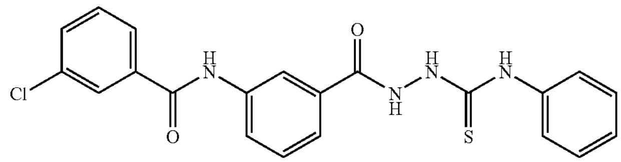 | 1-[3-(3-Chlorobenzamido)-benzoyl]-4-phenyl-thiosemicarbazide |
| 7 | 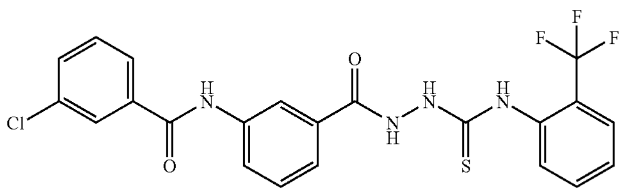 | 1-[3-(3-Chlorobenzamido)-benzoyl]-4-(2-trifluoromethylphenyl)-thiosemicarbazide |
| 8 | 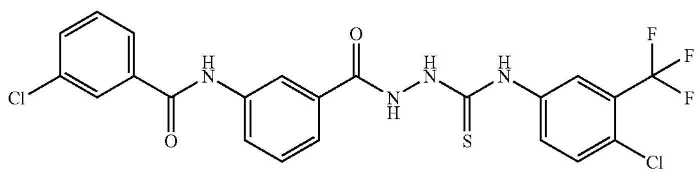 | 1-[3-(3-Chlorobenzamido)-benzoyl]-4-(4-chloro-3-trifluoromethyiphenyl)-thiosemicarbazide |
| 9 | 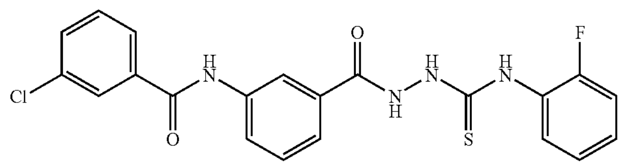 | 1-[3-(3-Chlorobenzamido)-benzoyl]-4-(2-fluorophenyl)-thiosemicarbazide |
| 10 | 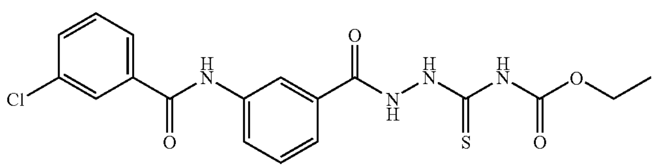 | 1-[3-(3-Chlorobenzamido)-benzoyl]-4-(ethoxycarbonyl-thiosemicarbazide |
| 11 | 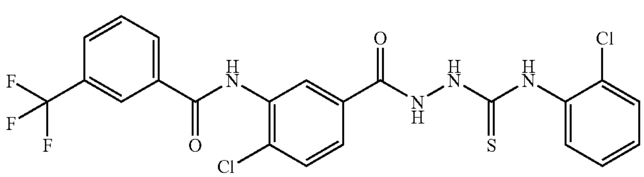 | 4-(2-Chlorophenyl)-1-[4-chloro-3-(3-trifluoromethylbenzamido)-benzoyl]-thiosemicarbazide |
| 12 | 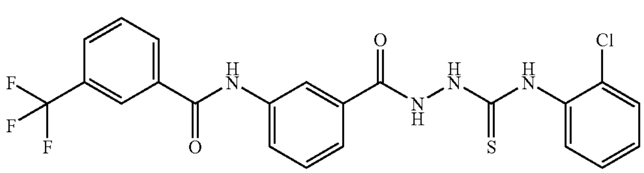 | 4-(2-Chlorophenyl)-1[3-(3-trifluoromethylbenzamido)-benzoyl]-thiosemicarbazide |
| 13 | 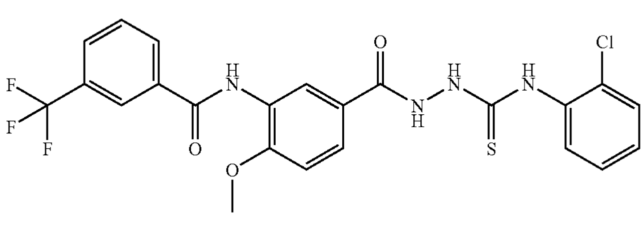 | 4-(2-Chlorophenyl)-1-[4-methoxy-3-(3-trifluoromethylbenzamido)-benzoyl]-thiosemicarbazide |

-continued

| | Structure | Chemical Name |
|---|---|---|
| 14 | 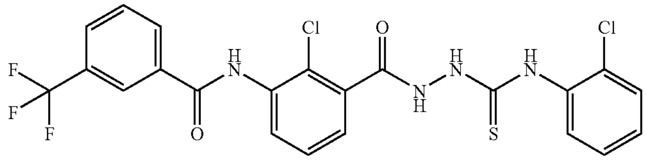 | 4-(2-Chlorophenyl)-1-[2-chloro-3-(3-trifluoromethylbenzamido)-benzoyl]-thiosemicarbazide |
| 15 | 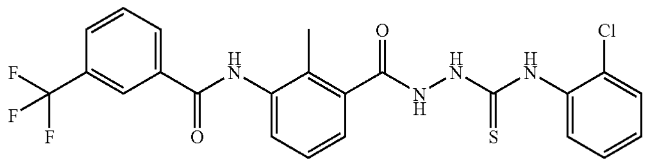 | 4-(2-Chlorophenyl)-1-[2-methyl-3-(3-trifluoromethylbenzamido)-benzoyl]-thiosemicarbazide |
| 16 | 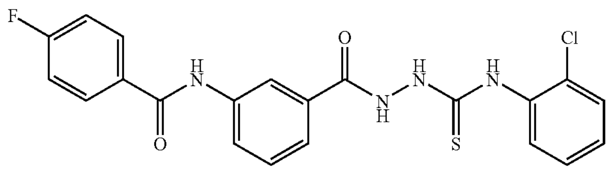 | 4-(2-Chlorophenyl)-1-[3-(4-fluorobenzamido)-benzoyl]-thiosemicarbazide |
| 17 | 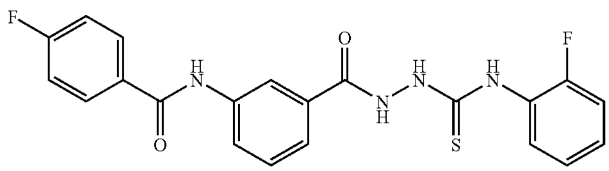 | 1-[3-(4-Fluorobenzamido)-benzoyl]-4-(2-fluorophenyl)-thiosemicarbazide |
| 18 | 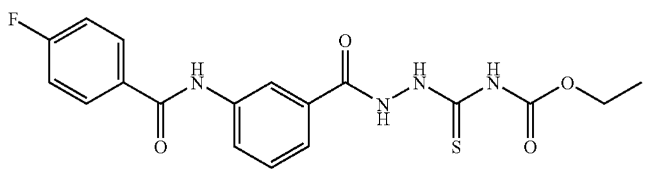 | 4-(Ethoxycarbonyl-1-[3-(4-fluorobenzamido)-benzoyl]-thiosemicarbazide |
| 19 | 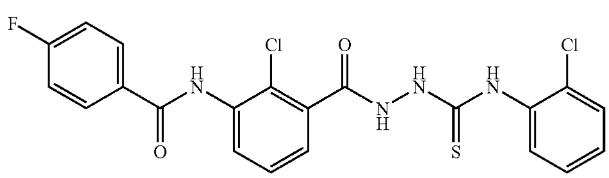 | 4-(2-Chlorophenyl)-1-[2-chloro-3-(4-fluorolbenzamido)-benzoyl]-thiosemicarbazide |
| 20 | 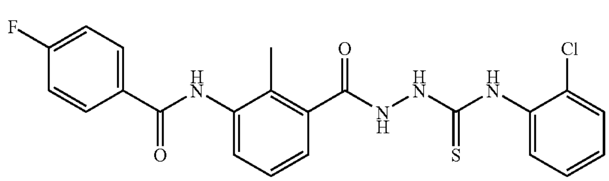 | 4-(2-Chlorophenyl)-1-[3-(4-fluorobenzamido)-2-methylbenzoyl]-thiosemicarbazide |
| 21 | 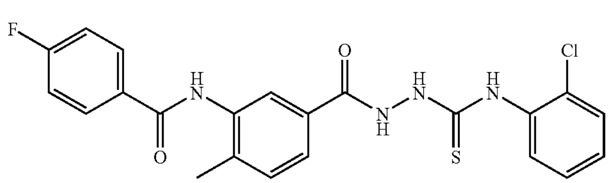 | 4-(2-Chlorophenyl)-1-[3-(4-fluorobenzamido)-4-methylbenzoyl]-thiosemicarbazide |

-continued

| | Structure | Chemical Name |
|---|---|---|
| 22 | 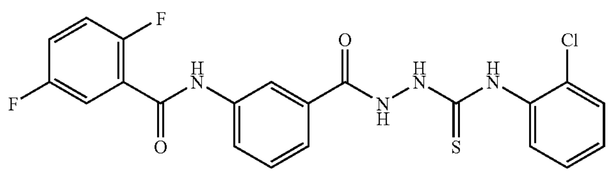 | 4-(2-Chlorophenyl)-1-[3-(2,5-difluorobenzamido)-benzoyl]-thiosemicarbazide |
| 23 | 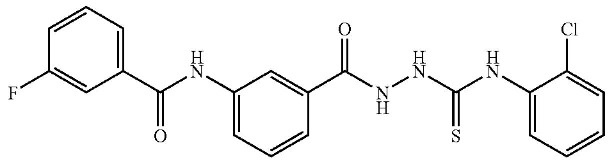 | 4-(2-Chlorophenyl)-1-[3-(3-fluorobenzamido)-benzoyl]-thiosemicarbazide |
| 24 | 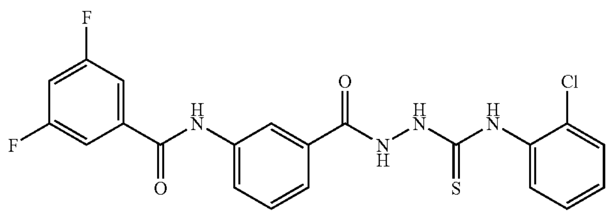 | 4-(2-Chlorophenyl)-1-[3-(3,5-difluorobenzamido)-benzoyl]-thiosemicarbazide |
| 25 | 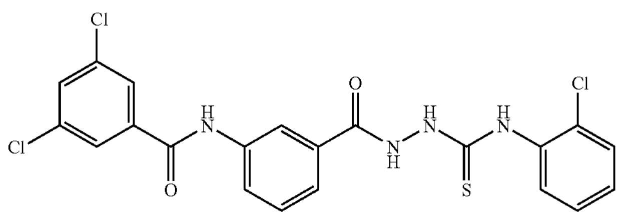 | 4-(2-Chlorophenyl)-1-[3-(3,5-dichlorobenzamido)-benzoyl]-thiosemicarbazide |
| 26 | 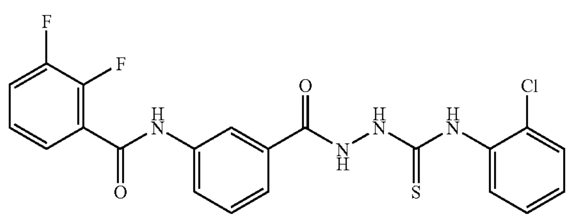 | 4-(2-Chlorophenyl)-1-[3-(2,3-difluorobenzamido)-benzoyl]-thiosemicarbazide |
| 27 | 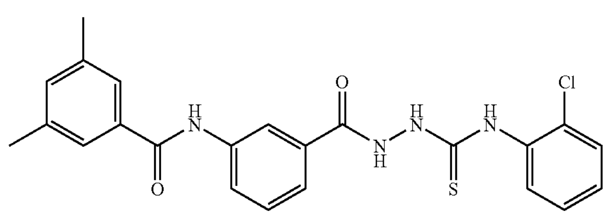 | 4-(2-Chlorophenyl)-1-[3-(3,5-dimethylbenzamido)-benzoyl]-thiosemicarbazide |
| 28 | 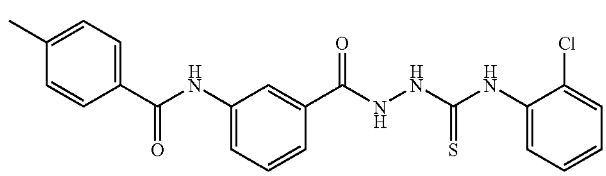 | 4-(2-Chlorophenyl)-1-[3-(4-methylbenzamido)-benzoyl]-thiosemicarbazide |

Salts. The compounds described herein and, optionally, all their isomers may be obtained in the form of their salts. Because some of the Formulas I and Ia have a basic center they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid. Within the scope of this invention, agrochemical or pharmaceutically acceptable salts are preferred.

3. Agrochemical Compositions and Use.

A. Herbicides. Active compounds of the present invention can be used to prepare agrochemical compositions and used as herbicides in like manner as other herbicidal compounds. See, e.g., U.S. Pat. No. 6,838,415; see also U.S. Pat. No. 6,861,389.

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

Monocotyledonous crops of the genera: *Oryza, Zea, Triticum, Hordeum, Avena, Secale, Sorghum, Panicum, Saccharum, Ananas, Asparagus, Allium.*

However, the use of the active compounds according to the invention is in no way restricted to these genera, but also extends in the same manner to other plants.

Depending on the concentration, the compounds according to the invention are suitable for total weed control, for example on industrial terrain and rail tracks and on paths and areas with or without tree growth. Equally, the compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the invention have herbicidal activity and activity when used on the soil and on above-ground parts of plants. To a certain extent they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amicarbazone, amidochlor, amidosulfuron, anilofos, asulam, atrazine, azafenidin, azimsulfueron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxy-fen, chloramben, chloridazon, chlorimuron(-ethyl), chlomitrofen, chlorosulftiron, chlorotoluron, cinidon(-ethyl), cinmethylin, cinosulfuron, clethodim, clodinafop(-propargyl), clomazone, clomeprop, clopyralid, clopyrasulfueron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuiron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfueron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, picolinafen, piperophos, pretilachlor primisulfueron(-methyl), procarbazone, prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quimnerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin, triflusulfuron and tritosuilfron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The present invention is explained in greater detail in the following non-limiting Examples.

EXAMPLE 1

Methyl 3-(3-chlorobenzamido)benzoate

To a solution of 15.1 gm (86 mmol) of 3-chlorobenzoyl chloride in 70 mL of dichloromethane was added 10.0 gm (66 mmol) of methyl 3-aminobenzoate. Triethylamine (9.38 gm, 13 mL, 93 mmol) was then added slowly to the mixture. After the addition was complete, the solution was warmed to 45° C. and stirred overnight. Ice was added to the solution to quench excess benzoyl chloride. After one hour, the layers were separated. The organic fraction was washed with 5% aqueous hydrochloride acid, saturated sodium bicarbonate, and finally with saturated sodium chloride solution. The dichloromethane solution was dried over magnesium sulfate. The drying agent was filtered off, and the solvent was removed by rotoevaporation to give the desired methyl 3-(3-chlorobenzamido)benzoate. $^1$H NMR (CDCl$_3$): δ3.91 (s, 3H), 7.61 (d of t, 1H), 7.78 (d of t, 1H, 7.87 (d of t, 1H), 8.40 (d of d, 1H), and 8.94 ppm (br s, 1H). MS m/z: 290.0 (M+H).

EXAMPLE 2

3-(3-Chlorobenzamido)benzhydrazide

To a solution of 1.0 gm (3.45 mmol) of methyl 3-(3-chlorobenzamido)benzoate in 24 mL of tetrahydrofuran was added 1.18 mL (34.5 mmol) of hydrazine hydrate. The reaction was heated overnight at 65° C. After cooling, the reaction mixture was concentrated under rotevaporation, and ether and water were added. The solid product was separated by filtration and dried in vacuo to give 3-(3-chlorobenzamido)benzhydrazide. MS m/z: 290.0 (M+H).

EXAMPLE 3

1-[3-(3-Chlorobenzamido)benzoyl]-4-(2-chlorophenyl)thiosemicarbazide (Compound 2)

To 200 mg (0.69 mmol) of 3-(3-chlorobenzamido)benzhydrazide in 2.5 mL of tetrahydrofuran was added 175 mg (135 μL, 1.04 mmol) of 2-chlorophenyl isothiocyanate. The reaction was stirred at room temperature overnight. After concentration by rotoevaporation, the residue was purified by preparative HPLC to give 243 mg (0.53 mmol, 77% yield) of 1-[3-(3-chlorobenzamido)benzoyl]-4-(2-chlorophenyl)thiosemicarbazide. $^1$H NMR (CDCl$_3$): δ7.28 (d of t, 1H), 7.35 (d of t, 1H), 7.99 (t, 1H), 8.34 (br s, 1H), and 8.98 ppm (br s, 1H). MS m/z: 459.0 (M+H).

EXAMPLE 4

Methyl 3-(3-trifluoromethylbenzamido)benzoate

To a solution of 17.9 gm (86 mmol) of 3-trifluoromethylbenzoyl chloride in 70 mL of dichloromethane was added 10.0 gm (66 mmol) of methyl 3-aminobenzoate. Triethylamine (9.38 gm, 13 mL, 93 mmol) was then added slowly to the mixture. After the addition was complete, the solution was warmed to 45° C. and stirred overnight. Ice was added to the solution to quench excess benzoyl chloride. After one hour, the layers were separated. The organic fraction was washed with 5% aqueous hydrochloride acid, saturated sodium bicarbonate, and finally with saturated sodium chloride solution. The dichloromethane solution was dried over magnesium sulfate. The drying agent was filtered off, and the solvent was removed by rotoevaporation to give the desired methyl 3-(3-trifluoromethylbenzamido)benzoate. $^1$H NMR (CDCl$_3$): δ3.92 (s. 3H), 7.52 (t, 1H), 7.74 (t, 1H), 7.80 (m, 1H), 7.92 (m, 1H), 7.96 (m, 1H), 8.21 (d, 1H), 8.26 (s, 1H), 8.43 (s, 1H), and 9.07 (br s, 1H). MS m/z: 324.0 (M+H).

EXAMPLE 5

3-(3-Trifluoromethylbenzamido)benzhydrazide

To a solution of 1.0 gm (3.09 mmol) of methyl 3-(3-trifluoromethylbenzamido)benzoate in 19 mL of tetrahydrofuran was added 1.06 mL (30.9 mmol) of hydrazine hydrate. The reaction was heated to reflux for 48 hr. After cooling, the reaction mixture was concentrated under rotevaporation, and ether and water were added. The solid product was separated by filtration and dried in vacuo to give 785 mg (2.43 mmol, 79% yield) of 3-(3-trifluoromethylbenzamido)benzhydrazide as a white solid. MS m/z: 324.0 (M+H).

EXAMPLE 6

4-(2-Chlorophenyl)-1-[3-(3-trifluoromethylbenzamido) benzoyl]thiosemicarbazide (Compound 12)

To 200 mg (0.62 mmol) of 3-(3-trifluoromethylbenzamido)benzhydrazide in 2.5 mL of tetrahydrofuran was added 157 mg (121 µL, 0.93 mmol) of 2-chlorophenyl isothiocyanate. The reaction was stirred at room temperature overnight. After concentration by rotoevaporation, the residue was purified by preparative HPLC to give 219 mg (0.44 mmol, 72% yield) of 4-(2-chlorophenyl)-1-[3-(3-trifluoromethylbenzamido)-benzoyl]thiosemicarbazide. $^1$H NMR (CDCl$_3$): δ7.28 (d of t, 1H), 7.36 (d of t, 1H), 7.49 (d of d, 1H), 7.55 (t, 1H), 7.69 (d, 2H), 7.74 (t, 1H), 7.94 (d of t, 2H), 8.21 (d, 1H), 8.27 (s, 1H), 8.36 (s, 1H), and 9.09 ppm (s, 1H). MS m/z: 493.0 (M+H).

EXAMPLE 7

Biological Screening

Plate-based in vivo screens were used to identify compounds with herbicidal activity. Three species of plants were used in screening: *Arabidopsis thaliana, Agrostis* sp. and *Nicotinia tabacum* (common tobacco). Test compounds in 1 µL of dimethylsulfoxide (DMSO) were delivered to individual wells of a 96-well microtiter plate. Growth media containing 10-15 seeds per 100 uL were then added. The growth media consisted of Murashige and Skoog Basal salt mixture, and 0.15% low melt agarose, all at a pH 6.2. The seeds remained neutrally buoyant and were easily pipettable at this concentration of low melt agarose. Each plate contained a column of untreated control wells in order to determine the false positive rate. The plates were covered and sealed and incubated at 27° C. for 8 days under continuous fluorescent lighting (155 umol/m$^2$/s). The plates were scored for herbicidal activity by visual inspection. Observed symptomology included growth inhibition, bleaching, leaf curling, and root growth inhibition. Six commercial herbicide standards were run concurrently with the experimental compounds as internal controls for assay sensitivity and plant response. The standards are described in Table 1 with their biochemical mode of action.

TABLE 1

Commercial herbicide standards.

| Herbicide | Class | Manufacturer | Mode of Action |
|---|---|---|---|
| Acifluorfen | Diphenyl Ether | BASF | Protoporphyrinogen Oxidase Inhibitor |
| Chlorsulfuron | Sulfonyl Urea | DuPont | ALS Inhibitor |
| Diuron | Urea | Various | Photosystem II Inhibitor |
| MCPA | Aryloxyalkonic acid | Various | Auxin mimic (Growth inhibitor) |
| Norflurazon | Pyridazinone | Syngenta | Phytoene Desaturase Inhibitor |
| Oryzalin | Dinitroanaline | Dow Agro | Microtubule Assembly Inhibitor |

The herbicidal activity of compositions in the present invention, presented as EC$_{90}$ concentrations in the *Arabidopsis thaliana* screen, is tabulated in Table 2.

TABLE 2

Herbicidal activity in the *Arabidopsis thaliana* screen

| Cmpd # | EC$_{90}$ (uM) |
|---|---|
| 2 | 0.1 |
| 3 | 3.3 |
| 4 | 0.3 |
| 6 | 0.15 |
| 7 | 1.2 |
| 9 | 0.05 |
| 11 | 3.3 |
| 12 | 0.3 |
| 14 | 0.3 |
| 22 | 0.05 |
| 23 | 0.05 |

The foregoing is illustrative of the present invention, and is not to be construed as limiting thereof. The invention is defined by the following claims, with equivalents of the claims to be included therein.

What is claimed is:
1. A compound of Formula Ia:

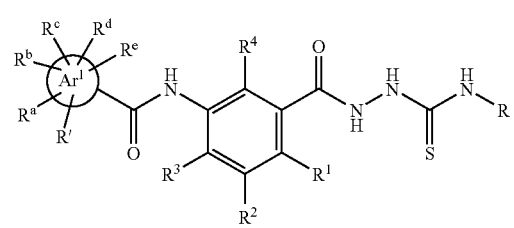

wherein:
Ar$^1$ is a five or six-membered aromatic ring selected from phenyl, pyridyl, pyrimidinyl, pyrazinyl, pyridazinyl, furyl, thienyl, oxazolyl, thiazolyl, isoxazolyl, isothiazolyl, pyrrolyl, imidazolyl, or pyrazolyl;
where R$^a$, R$^b$, R$^c$, R$^d$, and R$^e$ are, when present, each independently H, halogen, alkyl, alkenyl, alkynyl, haloalkyl, haloalkenyl, haloalkynyl, alkoxy, alkylthio, haloalkoxy, haloalkylthio, cyano, nitro, or aryl or heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro, or where two of the $R^a$, $R^b$, $R^c$, $R^d$, and $R^e$ are taken together to form another 5 or 6 membered ring containing C, N, O and/or S atoms, optionally substituted with halogen, alkyl, alkenyl, alkynyl, haloalkyl, haloalkenyl, haloalkynyl, alkoxy, alkylthio, haloalkoxy, haloalkylthio, cyano, or nitro, R' is, when present, H or alkyl, and R is alkyl, alkenyl, alkynyl, haloalkyl, haloalkenyl, haloalkynyl, acyl, or alkoxycarbonyl, or aryl optionally substituted with halogen, alkyl, alkenyl, alkynyl, haloalkyl, haloalkenyl, haloalkynyl, alkoxy, alkylthio, haloalkoxy, haloalkylthio, cyano, or nitro; or R is heteroaryl optionally substituted with halogen, alkyl, alkenyl, alkynyl, haloalkyl, haloalkenyl, haloalkynyl, alkoxy, alkylthio, haloalkoxy, haloalkylthio, cyano, or nitro;

$R^1$, $R^2$, and $R^3$ are each independently H, halogen, alkyl, alkenyl, alkynyl, haloalkyl, haloalkenyl, haloalkynyl, alkoxy, alkylthio, haloalkoxy, haloalkylthio, cyano, or nitro;

or a salt thereof.

2. A compound of claim 1 having the structure of Formula Ib:

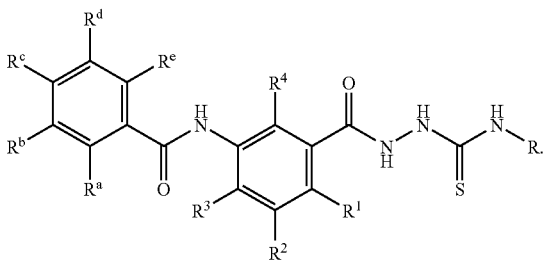

(Ib)

3. A compound of claim 2 wherein $R^a$, $R^b$, $R^c$, $R^d$, and $R^e$ are independently taken from H, halogen, alkyl, and haloalkyl.

4. A compound of claim 2 wherein $R^a$, $R^b$, $R^c$, $R^d$, and $R^e$ are independently taken from H, fluoro, chloro, methyl, and trifluoromethyl.

5. A compound of claim 2 wherein $R^1$, $R^2$, $R^3$, and $R^4$ are independently taken from H, halogen, alkyl, and alkoxy.

6. A compound of claim 2 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

7. A compound of claim 1 having the structure of Formula Ic:

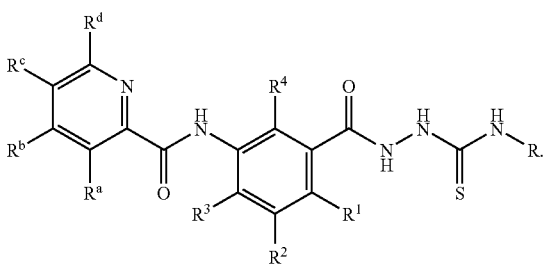

(Ic)

8. A compound of claim 7 wherein $R^a$, $R^b$, $R^c$, and $R^d$ are independently taken from H, halogen, alkyl, and haloalkyl.

9. A compound of claim 7 wherein $R^a$, $R^b$, $R^c$, and $R^d$ are independently taken from H, fluoro, chloro, methyl, and trifluoromethyl.

10. A compound of claim 7 wherein $R^1$, $R^2$, $R^3$, and $R^4$ are independently taken from H, halogen, alkyl, and alkoxy.

11. A compound of claim 7 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

12. A compound of claim 1 having the structure of Formula Id:

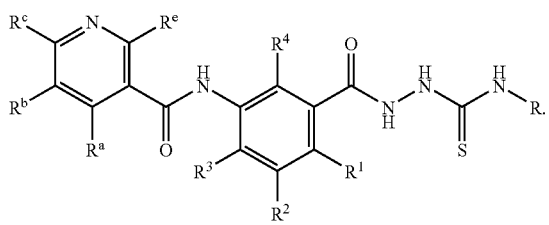

(Id)

13. A compound of claim 12 wherein $R^a$, $R^b$, $R^c$, and $R^e$ are independently taken from H, halogen, alkyl, and haloalkyl.

14. A compound of claim 12 wherein $R^a$, $R^b$, $R^c$, and $R^e$ are independently taken from H, fluoro, chloro, methyl, and trifluoromethyl.

15. A compound of claim 12 wherein $R^1$, $R^2$, $R^3$, and $R^4$ are independently taken from H, halogen, alkyl, and alkoxy.

16. A compound of claim 12 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

17. A compound of claim 1 having the structure of Formula Ie:

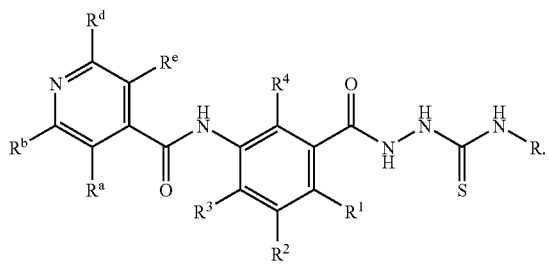

(Ie)

18. A compound of claim 17 wherein $R^a$, $R^b$, $R^d$, and $R^e$ are independently taken from H, halogen, alkyl, and haloalkyl.

19. A compound of claim 17 wherein $R^a$, $R^b$, $R^d$, and $R^e$ are independently taken from H, fluoro, chloro, methyl, and trifluoromethyl.

20. A compound of claim 17 wherein $R^1$, $R^2$, $R^3$, and $R^4$ are independently taken from H, halogen, alkyl, and alkoxy.

21. A compound of claim 17 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

22. A compound of claim 1, wherein $Ar^1$ is a five membered heteroaromatic ring containing 1, 2 or 3 heteroatoms selected from the group consisting of N, S, and O.

23. A compound of claim 1 having the structure of Formula If:

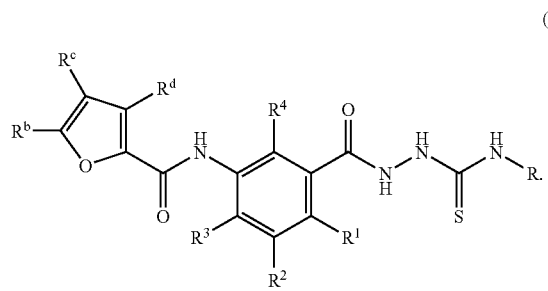 (If)

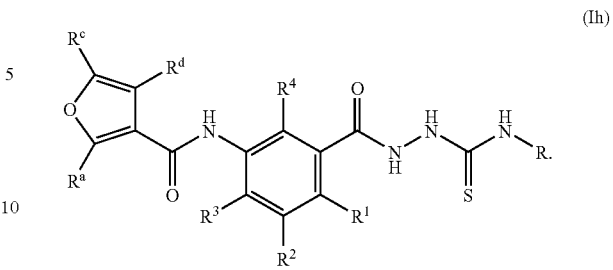 (Ih)

24. A compound of claim 23 wherein $R^b$, $R^c$, and $R^d$ are independently taken from H, halogen, alkyl, and haloalkyl.

25. A compound of claim 23 wherein $R^b$, $R^d$, and $R^e$ are independently taken from H, fluoro, chloro, methyl, and trifluoromethyl.

26. A compound of claim 23 wherein $R^1$, $R^2$, $R^3$, and $R^4$ are independently taken from H, halogen, alkyl, and alkoxy.

27. A compound of claim 23 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

28. A compound of claim 1 having the structure of Formula Ig:

34. A compound of claim 33 wherein $R^a$, $R^c$, $R^d$, and $R^e$ are independently taken from H, halogen, alkyl, and haloalkyl.

35. A compound of claim 33 wherein $R^a$, $R^c$, and $R^d$ are independently taken from H, fluoro, chloro, methyl, and trifluoromethyl.

36. A compound of claim 33 wherein $R^1$, $R^2$, $R^3$, and $R^4$ are independently taken from H, halogen, alkyl, and alkoxy.

37. A compound of claim 33 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

38. A compound of claim 1 having the structure of Formula Ii:

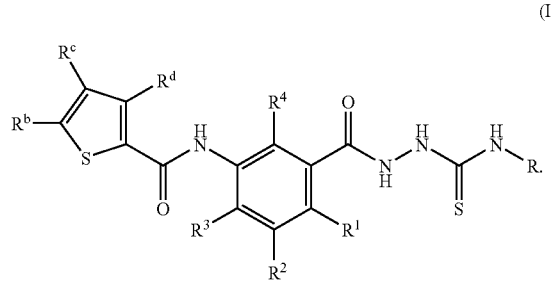 (Ig)

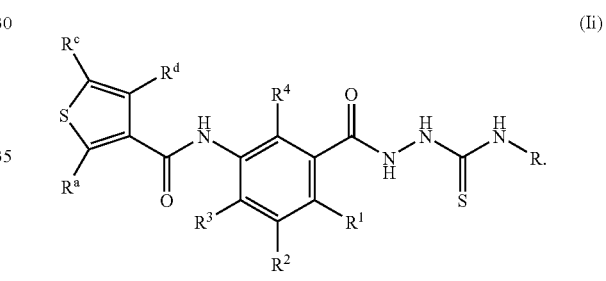 (Ii)

29. A compound of claim 28 wherein $R^b$, $R^c$, $R^d$ are independently taken from H, halogen, alkyl, and haloalkyl.

30. A compound of claim 28 wherein $R^b$, $R^c$, and $R^d$ are independently taken from H, fluoro, chloro, methyl, and trifluoromethyl.

31. A compound of claim 28 wherein $R^1$, $R^2$, $R^3$, and $R^4$ are independently taken from H, halogen, alkyl, and alkoxy.

32. A compound of claim 28 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

33. A compound of claim 1 having the structure of Formula Ih:

39. A compound of claim 38 wherein $R^a$, $R^c$, and $R^d$, are independently taken from H, halogen, alkyl, and haloalkyl.

40. A compound of claim 38 wherein $R^a$, $R^c$, and $R^d$ are independently taken from H, fluoro, chloro, methyl, and trifluoromethyl.

41. A compound of claim 38 wherein $R^1$, $R^2$, $R^3$, and $R^4$ are independently taken from H, halogen, alkyl, and alkoxy.

42. A compound of claim 38 wherein R is phenyl optionally substituted with halogen, alkyl, alkenyl, alkynyl, haloalkyl, haloalkenyl, haloalkynyl, alkoxy, alkylthio, haloalkoxy, haloalkylthio, cyano, or nitro.

43. A compound of claim 1 selected from the group consisting of:

| | Structure | Chemical Name |
|---|---|---|
| 1 | 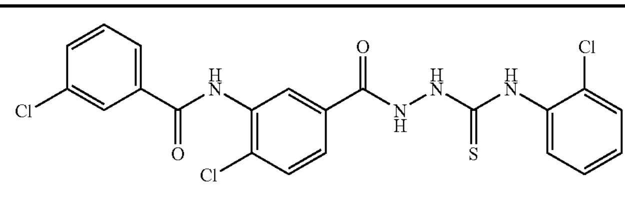 | 1-[4-Chloro-3-(3-chloro-benzamido)-benzoyl]-4-(2-chlorophenyl)-thiosemicarbazide |

-continued

| | Structure | Chemical Name |
|---|---|---|
| 2 | 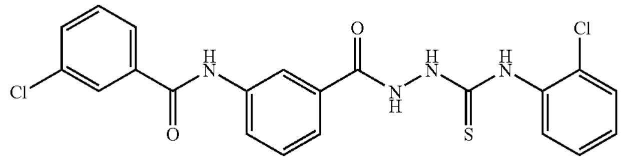 | 1-[3-(3-Chlorobenzamido)-benzoyl]-4-(2-chlorophenyl)-thiosemicarbazide |
| 3 | 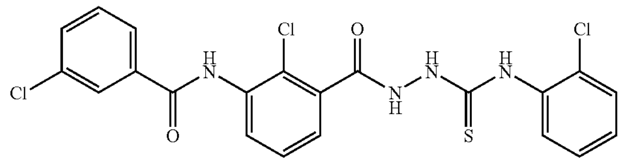 | 1-[2-Chloro-3-(3-chloro-benzamido)-benzoyl]-4-(2-chlorophenyl)-thiosemicarbazide |
| 4 | 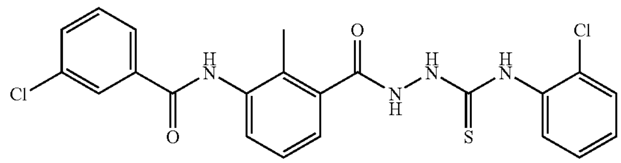 | 1-[3-(3-Chlorobenzamido)-2-methylbenzoyl]-4-(2-chloro-phenyl)-thiosemicarbazide |
| 5 | 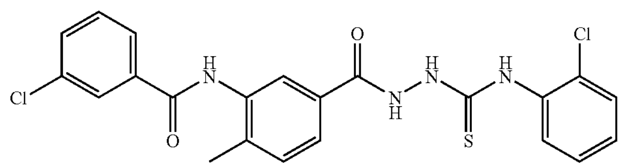 | 1-[3-(3-Chlorobenzamido)-4-methylbenzoyl]-4-(2-chlorophenyl)-thiosemicarbazide |
| 6 | 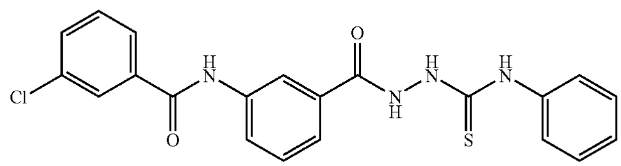 | 1-[3-(3-Chlorobenzamido)-benzoyl]-4-phenyl-thiosemicarbazide |
| 7 | 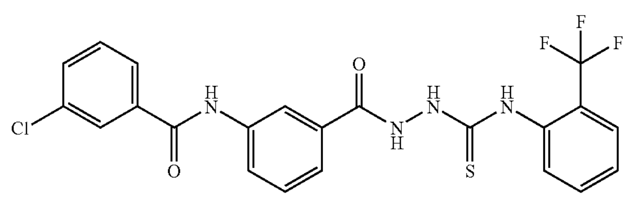 | 1-[3-(3-Chlorobenzamido)-benzoyl]-4-(2-trifluoromethylphenyl)-thiosemicarbazide |
| 8 | 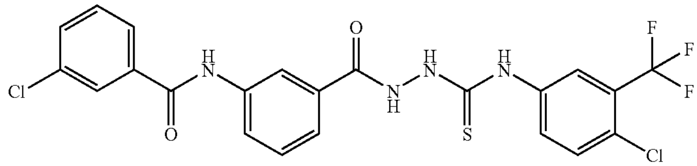 | 1-[3-(3-Chlorobenzamido)-benzoyl]-4-(4-chloro-3-trifluoromethylphenyl)-thiosemicarbazide |
| 9 | 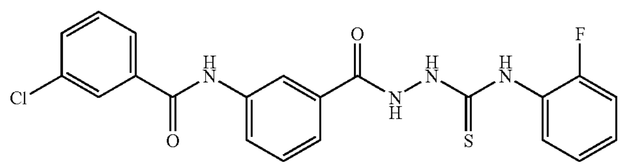 | 1-[3-(3-Chlorobenzamido)-benzoyl]-4-(2-fluorophenyl)-thiosemicarbazide |
| 10 | 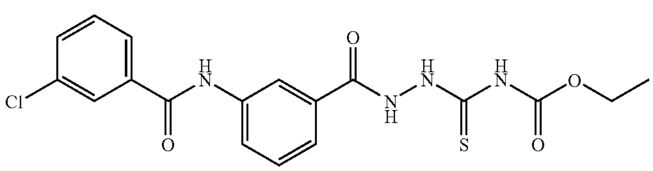 | 1-[3-(3-Chlorobenzamido)-benzoyl]-4-(ethoxycarbonyl-thiosemicarbazide |

| | Structure | Chemical Name |
|---|---|---|
| 11 | 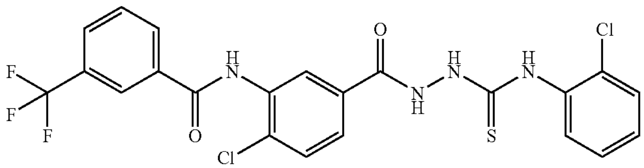 | 4-(2-Chlorophenyl)-1-[4-chloro-3-(3-trifluoromethylbenzamido)-benzoyl]-thiosemicarbazide |
| 12 | 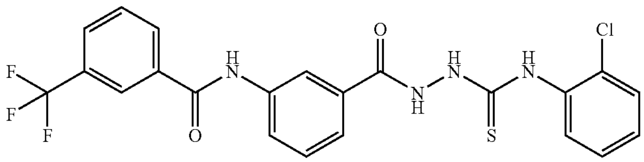 | 4-(2-Chlorophenyl)-1[3-(3-trifluoromethylbenzamido)-benzoyl]-thiosemicarbazide |
| 13 | 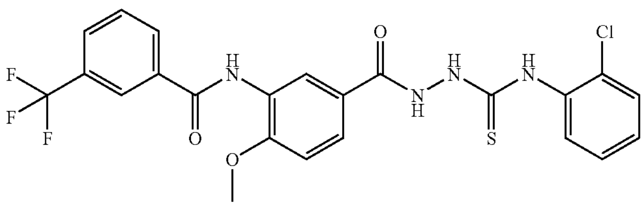 | 4-(2-Chlorophenyl)-1-[4-methoxy-3-(3-trifluoromethylbenzamido)-benzoyl]-thiosemicarbazide |
| 14 | 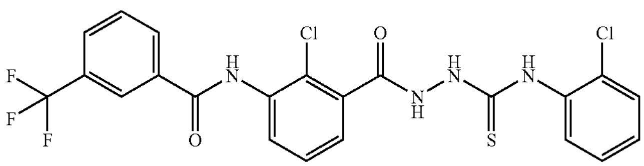 | 4-(2-Chlorophenyl)-1-[2-chloro-3-(3-trifluoromethylbenzamido)-benzoyl]-thiosemicarbazide |
| 15 | 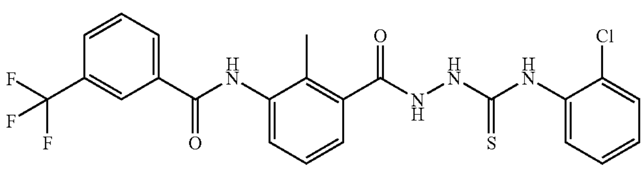 | 4-(2-Chlorophenyl)-1-[2-methyl-3-(3-trifluoromethylbenzamido)-benzoyl]-thiosemicarbazide |
| 16 | 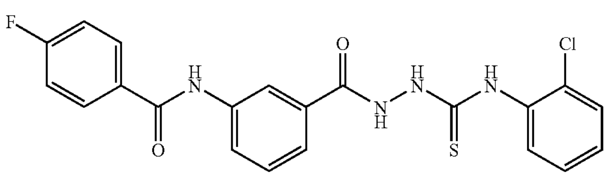 | 4-(2-Chlorophenyl)-1-[3-(4-fluorobenzamido)-benzoyl]-thiosemicarbazide |
| 17 | 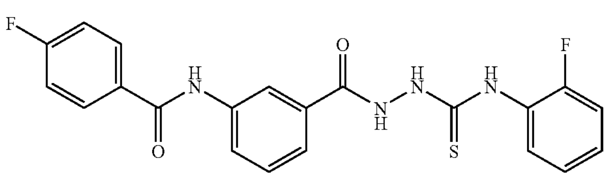 | 1-[3-(4-Fluorobenzamido)-benzoyl]-4-(2-fluorophenyl)-thiosemicarbazide |
| 18 | 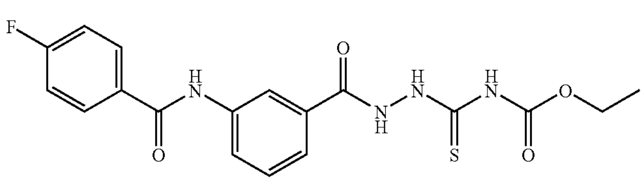 | 4-(Ethoxycarbonyl-1-[3-(4-fluorobenzamido)-benzoyl]-thiosemicarbazide |

| | Structure | Chemical Name |
|---|---|---|
| 19 | 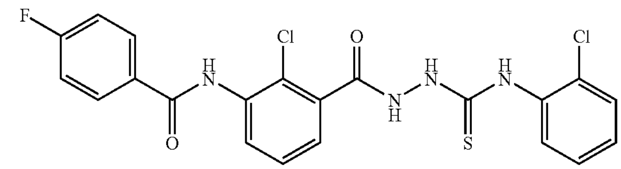 | 4-(2-Chlorophenyl)-1-[2-chloro-3-(4-fluorolbenzamido)-benzoyl]-thiosemicarbazide |
| 20 | 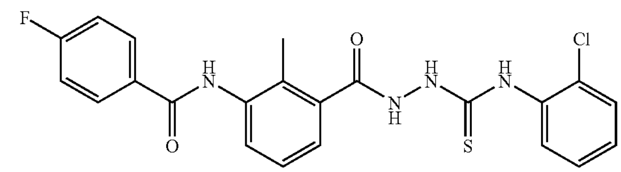 | 4-(2-Chlorophenyl)-1-[3-(4-fluorobenzamido)-2-methylbenzoyl]-thiosemicarbazide |
| 21 | 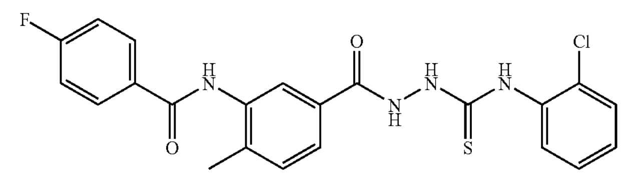 | 4-(2-Chlorophenyl)-1-[3-(4-fluorobenzamido)-4-methylbenzoyl]-thiosemicarbazide |
| 22 | 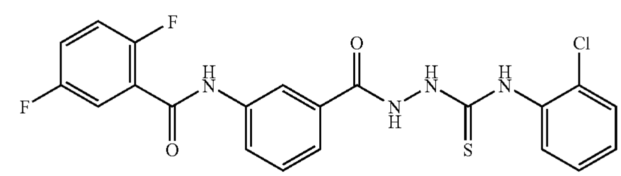 | 4-(2-Chlorophenyl)-1-[3-(2,5-difluorobenzamido)-benzoyl]-thiosemicarbazide |
| 23 | 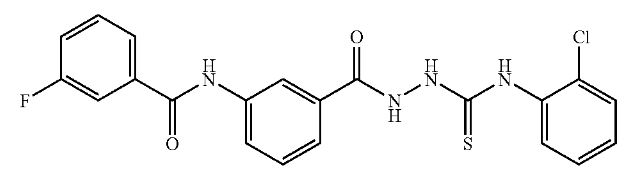 | 4-(2-Chlorophenyl)-1-[3-(3-fluorobenzamido)-benzoyl]-thiosemicarbazide |
| 24 | 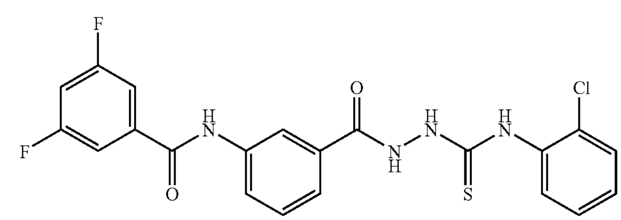 | 4-(2-Chlorophenyl)-1-[3-(3,5-difluorobenzamido)-benzoyl]-thiosemicarbazide |
| 25 | 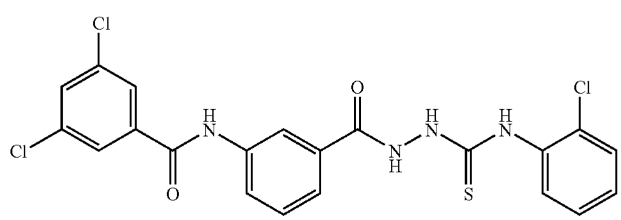 | 4-(2-Chlorophenyl)-1-[3-(3,5-dichlorobenzamido)-benzoyl]-thiosemicarbazide |
| 26 | 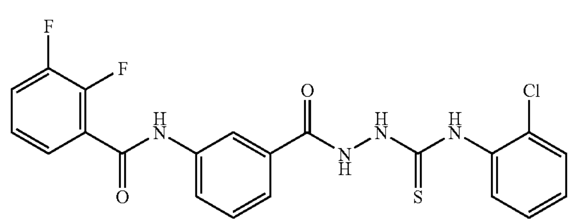 | 4-(2-Chlorophenyl)-1-[3-(2,3-difluorobenzamido)-benzoyl]-thiosemicarbazide |

-continued

| | Structure | Chemical Name |
|---|---|---|
| 27 | 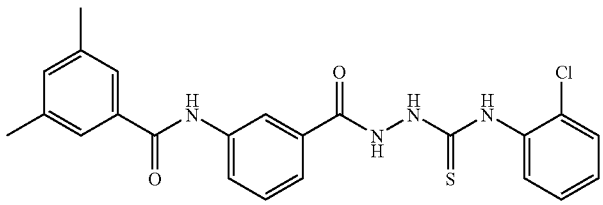 | 4-(2-Chlorophenyl)-1-[3-(3,5-dimethylbenzamido)-benzoyl]-thiosemicarbazide |
| 28 | | 4-(2-Chlorophenyl)-1-[3-(4-methylbenzamido)-benzoyl]-thiosemicarbazide | or a salt thereof.

44. A compound of claim 1 selected from the group consisting of:
1-[3-(3-Chlorobenzamido)-benzoyl]-4-(2-chlorophenyl)-thiosemicarbazide (compound 2);
1-[3-(3-Chlorobenzamido)-2-methylbenzoyl]-4-(2-chloro-phenyl)-thiosemicarbazide (compound 4);
1-[3-(3-Chlorobenzamido)-benzoyl]-4-phenyl-thiosemicarbazide (compound 6);
1-[3-(3-Chlorobenzamido)-benzoyl]-4-(2-trifluoromethylphenyl)-thiosemicarbazide (compound 7);
1-[3-(3-Chlorobenzamido)-benzoyl]-4-(2-fluorophenyl)-thiosemicarbazide (compound 9);
4-(2-Chlorophenyl)-1-[3-(3-trifluoromethylbenzamido)-benzoyl]-thiosemicarbazide (compound 12);
4-(2-Chlorophenyl)-1-[2-chloro-3-(3-trifluoromethylbenzamido)-benzoyl]-thiosemicarbazide (compound 14);
4-(2-Chlorophenyl)-1-[3-(4-fluorobenzamido)-benzoyl]-thiosemicarbazide (compound 16);
4-(Ethoxycarbonyl-1-[3-(4-fluorobenzamido)-benzoyl]-thiosemicarbazide (compound 18);
4-(2-Chlorophenyl)-1-[3-(2,5-difluorobenzamido)-benzoyl]-thiosemicarbazide (compound 22);
4-(2-Chlorophenyl)-1-[3-(3-fluorobenzamido)-benzoyl]-thiosemicarbazide (compound 23);
4-(2-Chlorophenyl)-1-[3-(3,5-difluorobenzamido)-benzoyl]-thiosemicarbazide (compound 24);
4-(2-Chlorophenyl)-1-[3-(3,5-dichlorobenzamido)-benzoyl]-thiosemicarbazide (compound 25);
4-(2-Chlorophenyl)-1-[3-(2,3-difluorobenzamido)-benzoyl]-thiosemicarbazide (compound 26);
4-(2-Chlorophenyl)-1-[3-(3,5-dimethylbenzamido)-benzoyl]-thiosemicarbazide (compound 27);
4-(2-Chlorophenyl)-1-[3-(4-methylbenzamido)-benzoyl]-thiosemicarbazide (compound 28);

or a salt thereof.

45. A herbicidal composition comprising at least one compound according to claim 1 and an extender or surfactant.

46. A method for controlling undesirable plants comprising applying an effective amount of a compound of claim 1 to said plants or a habitat of said plants.

* * * * *